United States Patent [19]

O'Neill et al.

[11] Patent Number: 5,459,239
[45] Date of Patent: Oct. 17, 1995

[54] PEPTIDE SEQUENCES AND ANTIPEPTIDE ANTISERA FOR DETECTING HUMAN CYCLOOXYGENASE-1 AND CYCLOOXYGENASE-2 PROTEINS

[75] Inventors: Gary O'Neill, Dollard des Ormeaux; Philip J. Vickers, Pierrefonds; Stacia Kargman, Hampstead; Jillian F. Evans, Brossard, all of Canada

[73] Assignee: Merck Frosst Canada Inc., Kirkland, Canada

[21] Appl. No.: 186,364

[22] Filed: Jan. 24, 1994

[51] Int. Cl.$^6$ ............... A61K 37/02; C07K 5/00; C07K 7/00; C07K 15/00

[52] U.S. Cl. ............ 530/327; 530/300; 530/812; 435/177; 435/43

[58] Field of Search ........................ 530/327, 300

OTHER PUBLICATIONS

Hla et al. 1992. Human cyclooxygenase–2 cDNA. PNAS. 89:7384–7388.

E. H. Eylar, et al, Methods in Enzymology, vol. XXII, pp. 123–130 (1971) "Isolation of Plasma Membranes from Mammalian Cells".

Devereux, J. et al. Nucleic Acids Res. 12:387–395 (1984).

Elroy–Stein, O. et al. Proc. Natl. Acad. Sci. 86:6126–6130 (1989).

Funk, C. D. et al. FASEB J. 5:2304–2312 (1991).

Harlow, E. et al. A Laboratory Manual, Cold Spring Harbor Laboratory, Cold Spring Harbor, New York (1988), pp. 72–87, 283–318, 553–612.

Laemmli, U.K. Nature 227:680–685 (1970).

Moss, B. et al. Nature 348:91–92 (1990).

Mumby, S. et al. J. Biol. Chem. 263:2020–2026 (1988).

Towbin, H. et al. Proc. Natl. Acad. Sci., USA 76:4350–4354 (1979).

Primary Examiner—Christine M. Nucker
Assistant Examiner—Nita M. Minnifield
Attorney, Agent, or Firm—Curtis C. Panzer; David L. Rose; Robert J. North

[57] ABSTRACT

This invention discloses novel immunogenic peptide sequences, derived from the human cyclooxygenase-1 and cyclooxygenase-2 cDNAs which elicit specific non cross-reactive antibody responses. Assays are also disclosed for selectively and independently detecting cyclooxygenase-1 or cyclooxygenase-2 proteins present in a given biological sample.

3 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:

( A ) LENGTH: 17 amino acids

```
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:1:

Thr  Ser  Met  Leu  Val  Asp  Tyr  Gly  Val  Glu  Ala  Leu  Val  Asp  Ala  Phe
        1                   5                        10                       15

Ser ( 2 ) INFORMATION FOR SEQ ID NO:2:

( i ) SEQUENCE CHARACTERISTICS:
            ( A ) LENGTH: 12 amino acids
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:2:

Asp  Asp  Ile  Asn  Pro  Thr  Val  Leu  Leu  Lys  Glu  Arg
        1                   5                        10
```

PEPTIDE SEQUENCES AND ANTIPEPTIDE ANTISERA FOR DETECTING HUMAN CYCLOOXYGENASE-1 AND CYCLOOXYGENASE-2 PROTEINS

BACKGROUND OF THE INVENTION

1. Field of the Invention

This invention relates to peptide sequences for the production of selective non-cross-reactive antipeptide antisera for the detection of human cyclooxygenase-1 and cyclooxygenase-2 proteins.

2. Brief Description of Disclosure in the Art

Non-steroidal, anti-inflammatory drugs exert many of their anti-inflammatory, analgesic, antipyretic activity through the inhibition of prostaglandin G/H synthase, also known as cyclooxygenase. Until recently, only one form of cyclooxygenase had been characterized, this corresponding to cyclooxygenase-1 (COX-1), a constitutive enzyme originally identified in bovine seminal vesicles and subsequently cloned from ovine, murine, and human sources. More recently the gene for an inducible form of cyclooxygenase (cyclooxygenase-2; COX-2), which is distinct from the cyclooxygenase-1, has been cloned, sequenced and characterized from chicken, murine, rat and human sources.

Cyclooxygenase-2 is rapidly and readily inducible by a number of agents including mitogens, endotoxin, hormones, cytokines and growth factors. Given that prostaglandins have both physiological and pathological roles, we have concluded that the constitutive enzyme, cyclooxygenase-1, is responsible for much of the endogenous basal release of prostaglandins and hence is important in their physiological functions which include the maintenance of gastrointestinal integrity and renal blood flow. In contrast the inducible form of the enzyme, cyclooxygenase-2, is mainly responsible for the pathological effects of prostaglandins where rapid induction of the enzyme would occur in response to inflammatory agents, hormones, growth factors, and cytokines. Currently, there are no reagents, such as specific polyclonal antisera or monoclonal antibodies, selective enough to permit the specific identification of the human COX-1 protein. To date, existing antisera developed have been cross-reactive, and react with both COX-1 and COX-2, thus rendering it difficult to distinguish between the two proteins. Mutually exclusive specific antibody reagents would greatly aid in the evaluation of the individual contributions of either COX-1 or COX-2 to pathological conditions.

Accordingly, it is an object of this invention to provide antibody reagents that permit the selective identification and quantification of cyclooxygenase-1 and cyclooxygenase-2 proteins in important biological preparations.

SUMMARY OF THE INVENTION

We have discovered that human COX-1 and COX-2 derived peptide segments are immunogenic, particularly when attached to a carrier protein, e.g. thyroglobulin, and will elicit the production of specific and non-cross reactive antisera to hCOX-1 and hCOX-2.

By this invention there is provided a human COX-1 protein derived peptide sequence: Thr-Ser-Met-Leu-Val-Asp-Tyr-Gly-Val-Glu-Ala-Leu-Val-Asp-Ala-Phe-Ser (Seq. Id. No. 1).

Further provided is a human COX-2 protein derived peptide sequence: Asp-Asp-Ile-Asn-Pro-Thr-Val-Leu-Leu-Lys-Glu-Arg (Seq. Id. No. 2).

We have also discovered, immunological non-cross reactive assays to specifically identify human cyclooxygenase-1 and cyclooxygenase-2 proteins in biological preparations.

Furthermore there is provided a method for detecting the presence of human COX-1 protein in a biological sample comprising the step of contacting the sample with the anti-COX-1 antisera and observing any binding between the human COX-1 protein and said anti-COX-1 antisera which is a positive indication of presence of human COX-1 protein in the sample.

Also provided is a method for detecting the presence of human COX-2 protein in a biological sample comprising the step of contacting sample with the anti-COX-2 antisera and observing any binding between the human COX-2 protein and said anti COX-2 antisera which is a positive indication of the presence of human COX-2 protein in the sample.

DETAILED DESCRIPTION OF THE INVENTION

The following abbreviations are used herein: ELISA, enzyme linked immunosorbent assay; h, human; hCOX-1, human cyclooxygenase-1 (a.k.a. prostaglandin Grid synthase-1); hCOX-2, human cyclooxygenase-2 (a.k.a. prostaglandin G/H synthase-2); PBS, phosphate buffered saline; RIA, radio immunoassay; SDS-PAGE, sodium dodecyl sulfate polyacrylamide gel electrophoresis.

The invention encompasses derived COX-1 and COX-2 peptide segment sequences for the production of antisera comprising the steps of:

(a) selection of unique COX-1 and COX-2 peptide sequences that will elicit a specific immune response;

(b) production of antisera in animals raised against the COX-1 and COX-2 peptides in step (a);

(c) immunological detection of COX-1 and COX-2 proteins in cell lines and/or tissues using the specific antipeptide antisera in step (b).

Further, the invention encompasses the peptide sequence Thr-Ser-Met-Leu-Val-Asp-Tyr-Gly-Val-Glu-Ala-Leu-Val-Asp-Ala-Phe-Ser (Seq. Id. No. 1) derived from human cyclooxygenase-1, or an obvious degenerate variation thereof.

Still further, another embodiment of the invention encompasses the peptide sequence Asp-Asp-Ile-Asn-Pro-Thr-Val-Leu-Leu-Lys-Glu-Arg (Seq. Id. No. 2) derived from human cyclooxygenase-2, or a degenerate variation thereof.

As will be appreciated by those of skill in the art, a substantial number of insignificant and trivial amino acid substitutions and changes can be made in a peptide that produce no significant effect on the immunogenicity or biological activity of the peptide. Accordingly, the invention also includes alternative peptide sequences wherein one or more amino acid (or amino acids) are replaced with another amino acid(s).

Identification of biological samples, e.g., cells, tissues or fluids, including sera, expressing cyclooxygenase-1 and cyclooxygenase-2 by detection with anti-cyclooxygenase-1 and anti-cyclooxygenase-2 antibodies may be done by several means, including but not limited to immunoblot analysis, enzyme linked immunosorbent assay (ELISA), and radioimmunometric assay.

Concentrations of cyclooxygenase-1 and cyclooxygenase-2 protein in either host cells or tissues are quantitated by immunoaffinity and/or ligand affinity techniques. Cyclooxygenase-1 and cyclooxygenase-2 specific affinity beads or cyclooxygenase-2 specific antibodies are used to isolate $^{35}$S-methionine-labeled or unlabeled cyclooxygenase-1 and cyclooxygenase-2 protein. Labeled cyclooxygenase-1 and/or cyclooxygenase-2 protein is analyzed by SDS-PAGE and/or immunoblotting. Unlabeled cyclooxygenase-1 and cyclooxygenase-2 protein is detected by immunoblotting, ELISA or RIA assays employing cyclooxygenase-1 and cyclooxygenase-2 specific antibodies, respectively.

The specific antipeptide antibodies to cyclooxygenase-1 and cyclooxygenase-2 may be employed for the purification of cyclooxygenase-1 and cyclooxygenase-2 from natural and recombinant sources. Cyclooxygenase-1 and cyclooxygenase-2 can be separated from other cellular proteins by use of an immunoaffinity column made with monoclonal or polyclonal antibodies specific for the COX-1 and/or COX-2 peptide sequences.

The following examples serve to illustrate the invention but do not limit the scope or spirit of it in any way:

EXAMPLE 1

Selection of immunogenic peptides for the production of specific anti-COX-1 and antiCOX-2 antisera The amino acid sequences for both human COX-1 and COX-2 have been deduced from the translation of the cloned cDNA sequences (Funk et al., FASEB J. 5:2304–2312 (1991 ); Hla and Neilson, Proc. Natl. Acad. Sci. 89:7384–7388 (1992)). An alignment of the amino acid sequences of hCOX-1 and hCOX-2 was generated using the "Bestfit" computer algorithm (Devereux et al., Nucleic Acids Res. 12:387–395 (1984)) which aligns sequences for maximal homology. The amino acids that am identical in COX-1 and COX-2 were deduced. In order to raise antisera specific either for COX-1 or COX-2, peptides unique to either enzyme were required to be selected. From the alignment it was apparent that a variety of peptides of 10 to 20 amino acids in length that were unique to either COX-1 or COX-2 could be chosen. The varity of peptide sequences unique to either COX-1 and COX-2 were analyzed for their potential immunogenicity using the "Antigenic" computer algorithm (Devereux et al., Nucleic Acids Res. 12:387–395 (1984)). On the basis of our analysis and individual interpretation of this data, the following peptide sequences were selected on a trial basis for the immunization and production of specific anti-peptide antisera to immunologically detect hCOX-1 and hCOX-2 proteins in a non cross-reactive manner.

The COX-1 specific peptide is located at amino acids 410 to 426, inclusive, of the COX-1 precursor protein and termed T17S (also identified herein as Seq. Id. No:1). The peptide T17S has no similarity to any peptide sequence of human cyclooxygenase-2. Peptide T17S is:

a) Threonine-Serine-Methionine-Leucine-Valine-Aspartate-Tyrosine-Glycine-Valine-Glutamate-Alanine-Leucine -Valine-Aspartate-Alanine-Phenylalanine-Serine b) In standard 3-letter amino acid abbreviation T17S is:
Thr-Ser-Met-Leu-Val-Asp-Tyr-Gly-Val-Glu-Ala-Leu-Val-Asp-Ala-Phe-Ser c) In standard 1-letter amino acid abbreviation T17S is: TSMLVDYGVEALVDAFS The COX-2 specific peptide is located at amino acids 589 to 600, inclusive, of the COX-2 precursor protein and is termed D12R (also identified herein as Seq. Id. No:2). The peptide D12R has no similarity to any peptide sequence of human cyclooxygenase-1. Peptide D12R is:

a) Aspartate-Aspartate-Isoleucine-Asparagine-Proline-Threonine-Valine-Leucine-Leucine-Lysine-Glutamate-Arginnine b) In standard 3-letter amino acid abbreviation D12R is:
Asp-Asp-Ile-Asn-Pro-Thr-Val-Leu-Leu-Lys-Glu-Arg c) In standard 1-letter amino acid abbreviation D12R is: DDINPTVLLKER

EXAMPLE 2

Synthesis Of COX-1 and COX-2 peptides conjugate to protein carders

Methods for the chemical synthesis of peptides and the covalent chemical crosslinking of peptides to carrier proteins are reviewed in Harlow, E. and Lane D., Antibodies: A Laboratory Manual, Cold Spring Harbor Laboratory (1988), pages 72 to 87. The peptides described here, T17S and D12R, were chemically synthesized and conjugated to a protein carder. Forty milligrams of each peptide were synthesized and their composition verified by amino acid analysis. Ten mg of each peptide was conjugated to 50 mg of the protein carder thyroglobulin using 10 mg of 1-ethyl-3-(3-dimethylaminopropyl)-carbodiimide for each coupling reaction.

Other protein carders applicable herein are keyhole limpet hemacyanin, bovine serum albumin, ovalbumin, mouse serum albumin, rabbit senan albumin, and the like.

EXAMPLE 3

Production of antipeptide antisera by immunization of rabbits with peptides conjugated to a carder protein Methods for the production of antipeptide antisera by immunization of rabbits with peptides conjugated to a carder protein are reviewed in Harlow, E. and Lane D., (supra), pages 92 to 138. Briefly, for each peptide-carder protein conjugate two NZW female rabbits were pre-bled on day 0 of the immunization regimen to obtain pre-immune control antisera. Each rabbit was then intradermally injected at multiple sites on the back with 1 ml of Freund's complete adjuvant containing 250 μg of the peptide-protein carder conjugate. Twenty-one days after the primary injection, the rabbits were boosted by subcutaneous injection at multiple sites on the hind flanks with 250 μg of peptide-protein carder conjugate in 0.5 ml of Freund's incomplete adjuvant. Every 14 days following this boost the rabbits were test bled for 5 ml of immune sera, immediately followed by a booster immunization of 125 micrograms of the peptide-carrier conjugate in Freund's incomplete adjuvant. Following a test bleed, the titer of the antisera to the peptide was determined by ELISA.

EXAMPLE 4

Titering antipeptide antisera by ELISA and peptide affinity purification of the antisera Methods for the titering of antipeptide antisera by ELISA and the affinity purification of the antisera by peptide affinity chromatography are reviewed in Harlow, E. and Lane D., (supra), pages 283–318, and 553–612. Briefly, the peptides D12R and T175 were resuspended in PBS to a fmal concentration of 20 μg/ml. Fifty μL of the diluted peptide were used to coat the wells of a 96 well plastic microtiter dish by incubation at 23° C. for 2 hours. The peptide solution was removed and the microtiter plate washed thoroughly with PBS. Each well of the microtiter plate was then blocked to prevent nonspecific adsorption by incubation for 30 min at 37° C. with 250 μL of a 3% solution of bovine serum albumin (BSA) in PBS containing 0.05% TWEEN-20. The blocking solution was then removed and 50 μL of a 1:2 serial dilution starting at a 1:100 fold dilution of the test bleed in PBS containing 1% BSA was applied to each well and incubated for 1 hour at 37° C. The primary antisera test bleed was removed and then the plate was washed extensively with PBS containing 0.05% Tween 20 to remove unbound proteins. Wells that contained bound antibody were detected using a biotinylated goat anti-rabbit IgG streptavidin-alkaline phosphatase detection system as described by the manufacturer (BRL-GIBCO, Burlington, Ontario, Canada).

The method of antibody affinity purification is essentially as described previously (Mumby, S., Pang et al., J. Biol. Chem. 263:2020–2026 (1988)). The anti-peptide antisera were purified by affinity chromatography on immobilized peptide columns using the matrix Sepharose 4B according to the manufacturer's instructions (Pharmacia, Montreal, Quebec, Canada). Briefly, 15 mg of the peptides D12R and T17S were dissolved in 10 mL of 0.1M $NaHCO_3$ containing 0.5M NaCl. Two grams of the cyanogen bromide activated matrix S4B were swollen in 1 mM HCl, then mixed with the peptide dissolved in 0.1M $NaHCO_3$ containing 0.5M NaCl, and then gently mixed for two hours at 4° C. The gel slurry was transferred to a Buchner funnel and the remaining active groups were blocked by washing with 1M ethanolamine, followed by 0.1M sodium acetate, pH 4, containing 0.5M sodium chloride, and then PBS.

The antisera was prepared for affinity purification on the peptide-Sepharose 4B columns by first removing particulate matter from the antisera by centrifugation at 14,000×g for 1 min at room temperature. 2.0 mls of the cleared antisera were diluted 3-fold in wash buffer (20 mM Tris-HCl, pH 7.5; 0.1M NaCl) and the diluted antisera was passed twice over 1.0 ml of peptide-Sepharose 4B packed in a 0.7 by 4-cm Econocolumn (Bio-Rad). The column was washed with 20 mls of wash buffer and the antibodies were eluted with 10 mls of 0.1M glycine, pH 2.5. 1.0 ml fractions were collected into robes containing 0.1 ml 1M Tris-HCl, pH 8, to neutralize the glycine. Fractions containing protein (determined by spectrophotometry at 280 nm) were pooled and dialyzed against PBS. Affinity purified antibody activity against the appropriate peptide (i.e. T17S or D12R) was determined by ELISA as described above.

EXAMPLE 5

Detection of recombinant human COX-1 and COX-2 proteins and purified ovine COX-1 and COX-2 by immunoblot analysis using antipeptide antiSera Methods for the immunoblot detection of proteins using antipeptide antisera are reviewed in Harlow, E. and Lane D., (supra). The immunoblot procedure was used to verify that the antipeptide antisera detected either COX-1 or COX-2 and did not cross-react. The sources of COX protein were purified ram seminal vesicle COX-1 (Cayman Chemical Co., Ann Arbor, MI), purified sheep placental COX-2 (Cayman) and recombinant human COX-1 and COX-2. The production and preparation of microsomes containing recombinant hCOX-1 and hCOX-2 is described below.

In order to test the specificity of the polyclonal COX antisera, the ability of the antisera to specifically detect human COX protein was determined by immunoblot analysis. The source of human COX-1 and COX-2 were COS-7 monkey kidney cells infected with recombinant vaccinia viruses containing either the cDNA for human COX-1 or COX-2. Since both COX-1 and COX-2 have been shown to be associated with the cellular membranes and not the soluble cellular proteins, enriched COX-1 or COX-2 preparations were made by differential ultra-centrifugation in order to separate the soluble cellular proteins from the less soluble membrane proteins. Briefly, cells expressing either human COX-1 or COX-2 were harvested and disrupted by sonication. Unbroken cells, nuclei, and mitochondria were pelleted by a low speed centrifugation for 10 min at 10,0000×g at 4 degrees C. and discarded. The remaining supernatant, termed cell lysate, contains both the soluble cellular proteins and the less soluble membrane-derived components including COX-1 and COX-2. The membrane fraction is separated form the soluble fraction by centrifugation of the total cell lysate using centrifugal force of at least 100,000×g for 60 to 90 minutes. Under these conditions the soluble proteins remain in solution and the membrane proteins, including COX-1 and COX-2, are pelleted to the bottom of the centrifugation tube. Following the high speed centrifugation the supernatant containing the soluble protein fraction is decanted and discarded. The 100,000×g high speed centrifugation pellet containing the membrane proteins is relatively insoluble in aqueous buffers and must be resuspended by either vigorous pipetting, stirring, or sonication. During the resuspension procedure microsomes are formed by revesiculation of the fragmented plasma membranes. The microsomes are approximately 3 to 20 micrometers in diameter and thus are only a fraction of the size of the original membrane. Following resuspension, the 100,00×g high speed centrifugation pellet is referred to as the microsomal fraction or microsomes.

Briefly, recombinant human COX-1 and COX-2 were produced using a vaccinia virus expression system. The vaccinia system used here requires co-infection with two recombinant viruses (Moss et al, Nature 348:91–92 (1990)). One recombinant virus, VV:TF7-3 contains the bacteriophage T7 RNA polymerase gene under the control of the vaccinia virus P7.5 promoter (Elroy-Stein et al., Proc. Natl. Acad. Sci. 86:6126–6130 (1989)). The second recombinant virus contains either the hCOX-1 or hCOX-2 sequences flanked by the T7 promoter. Two recombinant vaccinia viruses were generated and designated VV:hCOX-1 (vaccinia containing the hCOX-1 open reading frame and 3' untranslated region), and VV:hCOX-2-3'fl(vaccinia containing the hCOX-2 open reading frame and the hCOX-1 3' untranslated region). Monolayer cultures of confluent COS-7 cells were co-infected with either VV:hCOX-1 or VV:hCOX2 and the helper VV:TF7-3, each at multiplicity of infection of 10. At various times post-infection, cells were harvested by scraping, washed twice with PBS, and resuspended in lysis buffer (100 mM Tris, pH 7.4, 10 mM EDTA, 2 mM phenylmethylsulfonylfluoride, 2 μg/ml leupeptin, 2 μg/ml aprotinin, and 2 μg/ml soybean trypsin inhibitor), and then disrupted using a microsonic cell disruptor (Cole-Parmer). Samples were centrifuged for 10 min at 10,000×g at 4° C. and the resulting supernatant was centrifuged for 90 min at 100,000×g at 4° C. The 100,000×g microsome fraction was resuspended in 100 mM Tris, pH 7.4, 10 mM EDTA, to yield a protein concentration of 1 to 3 mg/ml. Protein concentrations were determined using the Bio-Rad protein assay (Richmond, Calif.) with bovine serum albumin as standard.

The samples containing COX antigen were mixed with 0.5 vol SDS sample buffer (20 mM Tris-HCl, pH 6.8, containing 0.4% (w/v) SDS, 4% glycerol, 0.24M β-mercaptoethanol, and bromophenol blue), boiled for 5 min and subjected to SDS-PAGE on 9×10 cm precast 10% Tris-glycine acrylamide gels (Novex, San Diego, Calif.) according to the method of Laemmli (Laemmli, U.K. Nature 227:680–685 (1970)). Proteins were electrophoretically transferred to nitrocellulose membranes as described previously (Towbin, H. et al., Proc. Natl. Acad. Sci, U.S.A. 76, 4350–4354). Immunoblot analysis was carried out using the ECL (enhanced chemiluminescence) detection system essentially as described by Amersham (Oakville, Ontario, Canada). After transfer, nonspecific sites on the membrane were blocked with 3% dry skim milk powder in 20 mM Tris-HCl, pH 7.5, 500 mM NaCl, 0.1% (v/v) Tween 20 for 1 hour at room temperature, and then the membranes were washed two times in the same buffer for 5 min each. B lots were then incubated with a 1:000 final dilution of affinity purified anti-T17S peptide antiserum or affinity purified anti-D12R peptide antiserum in 1% dry skim milk in 20 mM Tris-HCl, pH 7.5, 500 mM NaCl, containing 0.05% (v/v) Tween 20 for 1 hour at room temperature. After washing the blot three times in 20 mM Tris-HCl, pH 7.5, 500 mM NaCl 0.1% (v/v) Tween 20, membranes were incubated with a 1:2000 final dilution of horse radish peroxidase-linked goat anti-rabbit antiserum (Amersham) in 1% dry skim milk in 20 mM Tris-HCl, pH 7.5, 500 mM NaCl, containing 0.05% (v/v) Tween 20 for 1 hour at room temperature. Blots were washed three times in 20 mM TrisHCl, pH 7.5, 500 mM NaCl, containing 0.3% (v/v) Tween 20, three times in 20 mM TrisHCl, pH 7.5, 500 mM NaCl, containing 0.05% (v/v) Tween 20 and then placed in 20 mM Tris-HCl, pH 7.5, 500 mM NaCl, prior to detection. An equal volume of each detection reagent was mixed and added to damp membranes for 1 min. Excess reagent was removed, blots were blotted dry and then exposed to Kodak XAR-5 film for between 5 seconds and 1 hour.

Immunoblot analysis using the rabbit anti-T17S peptide antiserum.

COS-7 cells were infected with VV:hCOX-1 and/or VV:TF7-3, grown for 24 h, harvested, and then used for the preparation of microsomes as described above. Samples were separated by SDS-PAGE, transferred to nitrocellulose, and immunoblotted with the anti-T17S peptide antiserum as described above. The immunoblot was developed using enhanced chemiluminescence as described above and exposed to autoradiographic film.

Results: Affinity purified anti-T17S peptide antiserum specifically detected purified ram seminal vesicle COX-1 (Cayman Chemical Co., Ann Arbor, Mich.) and human COX-1 expressed in vaccinia virus-infected COS cells as an approximate 72 kilodalton molecular weight species. In contrast, affinity purified anti-T17S antiserum did not detect either purified sheep placenta COX-2 (Cayman) or recombinant human COX-2 expressed in vaccinia virus infected-COS cells.

Immunoblot analysis using the rabbit anti-D12R peptide antiserum.

COS-7 cells were infected with VV:hCOX-2 and/or VV:TF7-3, grown for 24 h, harvested, and then used for the preparation of microsomes as described above. Samples were separated by SDS-PAGE, transferred to nitrocellulose, and immunoblotted with the anti-D12R peptide antiserum as described above. The immunoblot was developed using enhanced chemiluminescence as described in the text and exposed to automdiographic film.

Results: Affinity purified anti-D12R peptide antiserum detected purified sheep placenta COX-2 (Cayman) and recombinant human COX-2 expressed in vaccinia virus-infected COS cells. In contrast, affinity purified anti-D 12R peptide antiserum did not detect either purified ram seminal vesicle COX-1 or human COX-1 expressed in virus infected-COS cells. These results demonstrate that the affinity purified anti-T17S peptide antiserum and the affinity purified anti-D12R peptide antiserum can immunologically detect COX protein in a selective manner.

References cited herein are:

Devereux, J., Haerberli, P., and O. Smithies. A comprehensive set of sequence analysis programs for the VAX. Nucleic Acids Res. 12: 387–395 (1984)

Elroy-Stein, O., Fuerst, T. R., and B. Moss. Cap-independent translation of mRNA conferred by encephalomyocarditis virus 5' sequence improves the performance of the vaccinia/bacteriophage T7 hybrid expression system. Proc. Natl. Acad. Sci. 86: 6126–6130 (1989)

Funk, C. D., Funk, L. B., Kennedy, M. E., Pong, A. S., and G. A. Fitzgerald. Human platelet/erythroleukemia cell prostaglandin G/H synthase: cDNA cloning, expression, and gene chromosomal assignment. FASEB J. 5: 2304–2312 (1991)

Harlow, E. and Lane D., Antibodies: A Laboratory Manual, Cold Spring Harbor Laboratory, Cold Spring Harbor, New York (1988), pages 72–87, 283–318, 553–612

Hla, T., and K. Neilson. Human cyclooxygenase-2 cDNA. Proc. Natl. Acad. Sci. 89: 7384–7388 (1992)

Laemmli, U.K. Cleavage of structural proteins during assembly of the head of bacteriophage T4. Nature 227: 680–685 (1970)

Moss, B, Elroy-Stein, 0., Mizukami, T., Alexander, W. A., and T. R. Fuerst. New mammalian expression vectors. Nature 348: 91–92 (1990)

Mumby, S., Pang, I.-H., Gilman, A. G., and P. C. Stemweis. Chromatographic resolution and immunologic identification of the alpha40 and alpha41 subunits of guanine nucleotide-binding regulatory proteins from bovine brain. J. Biol. Chem. 263: 2020–2026 (1988)

Towbin, H. Staehelin, T., and J. Gordon. Electrophoretic transfer of proteins from polyacrylamide gels to nitrocellulose sheets: Procedure and some applications. Proc. Natl. Acad. Sci, U.S.A. 76: 4350–4354

What is claimed is:

1. A human COX-2 protein derived peptide having the sequence: Asp-Asp-Ile-Pro-Thr-Val-Leu-Leu-Lys-Glu-Arg (Seq. Id. No.2).

2. The peptide sequence of claim 1 conjugated to a carrier protein.

3. The peptide sequence of claim 2 wherein said carder protein is thyroglobulin.

* * * * *